United States Patent [19]

Mauldin

[11] Patent Number: 4,568,663
[45] Date of Patent: Feb. 4, 1986

[54] COBALT CATALYSTS FOR THE CONVERSION OF METHANOL TO HYDROCARBONS AND FOR FISCHER-TROPSCH SYNTHESIS

[75] Inventor: Charles H. Mauldin, Baton Rouge, La.

[73] Assignee: Exxon Research and Engineering Co., Florham Park, N.J.

[21] Appl. No.: 626,022

[22] Filed: Jun. 29, 1984

[51] Int. Cl.$^4$ .................. B01J 21/06; B01J 23/12; B01J 23/36; B01J 23/74
[52] U.S. Cl. ............................. 502/325; 518/715; 585/733
[58] Field of Search .............. 502/300, 325, 332, 350; 518/715

[56] References Cited

U.S. PATENT DOCUMENTS

| | | | |
|---|---|---|---|
| 2,539,847 | 1/1951 | McGrath | 518/715 |
| 3,389,965 | 6/1968 | Ruiter et al. | 502/332 X |
| 4,088,671 | 5/1978 | Kobylinski | 260/449 |
| 4,136,127 | 1/1979 | Antos | 260/668 D |
| 4,338,089 | 7/1982 | Schaper et al. | 518/707 |
| 4,385,193 | 5/1983 | Bijwaard et al. | 585/310 |

FOREIGN PATENT DOCUMENTS

| | | | |
|---|---|---|---|
| 2073237 | 3/1981 | United Kingdom | 332/385 |
| 610558 | 11/1978 | U.S.S.R. | 502/332 |

OTHER PUBLICATIONS

Chemical Abstracts, vol. 96, p. 170, Item 183828a (1982).
92:129385h; The Synthesis of Solid Hydrocarbons from Methanol; Shima, Kensuke, Morita, Tauyoshi (Miyazaki Univ., Miyazaki, Japan); Nouveau Journal De-Chime, vol. 6, No. 10-1982, p. 459.
Fischer-Tropsch Synthesis of Hydrocarbons Over Ruthenium Supported on Transition Metal Oxides; Kikuchi, Nomura, Matsumoto and Morita (Waseda University, Tokyo 160); Pan-Pacific Synfuels Conference, vol. I, Nov. 17-19, 1982 Tokyo, pp. 1-10.
Fischer-Tropsch Synthesis Over Titania-Supported Ruthenium Catalysts; Kikuchi, Matsumoto, Takahashi, Machino and Morita (Waseda University, 3-4-1 Okubo, Shinjuku, Tokyo, Japan); Printed in the Netherlands; Applied Catalysis, 10 (1984), pp. 251-260.

*Primary Examiner*—W. J. Shine
*Attorney, Agent, or Firm*—Llewellyn A. Proctor

[57] ABSTRACT

A rhenium promoted cobalt catalyst, especially a rhenium and thoria promoted cobalt catalyst, and process for the conversion of methanol to hydrocarbons. Methanol is contacted, preferably with added hydrogen, over said catalyst, or synthesis gas is contacted over said catalyst to produce, at reaction conditions, an admixture of $C_{10}+$ linear paraffins and olefins. These hydrocarbons can be further refined to high quality middle distillate fuels, and other valuable products such as mogas, diesel fuel, jet fuel, lubes and speciality solvents, particularly premium middle distillate fuels of carbon number ranging from about $C_{10}$ to about $C_{20}$.

20 Claims, 5 Drawing Figures

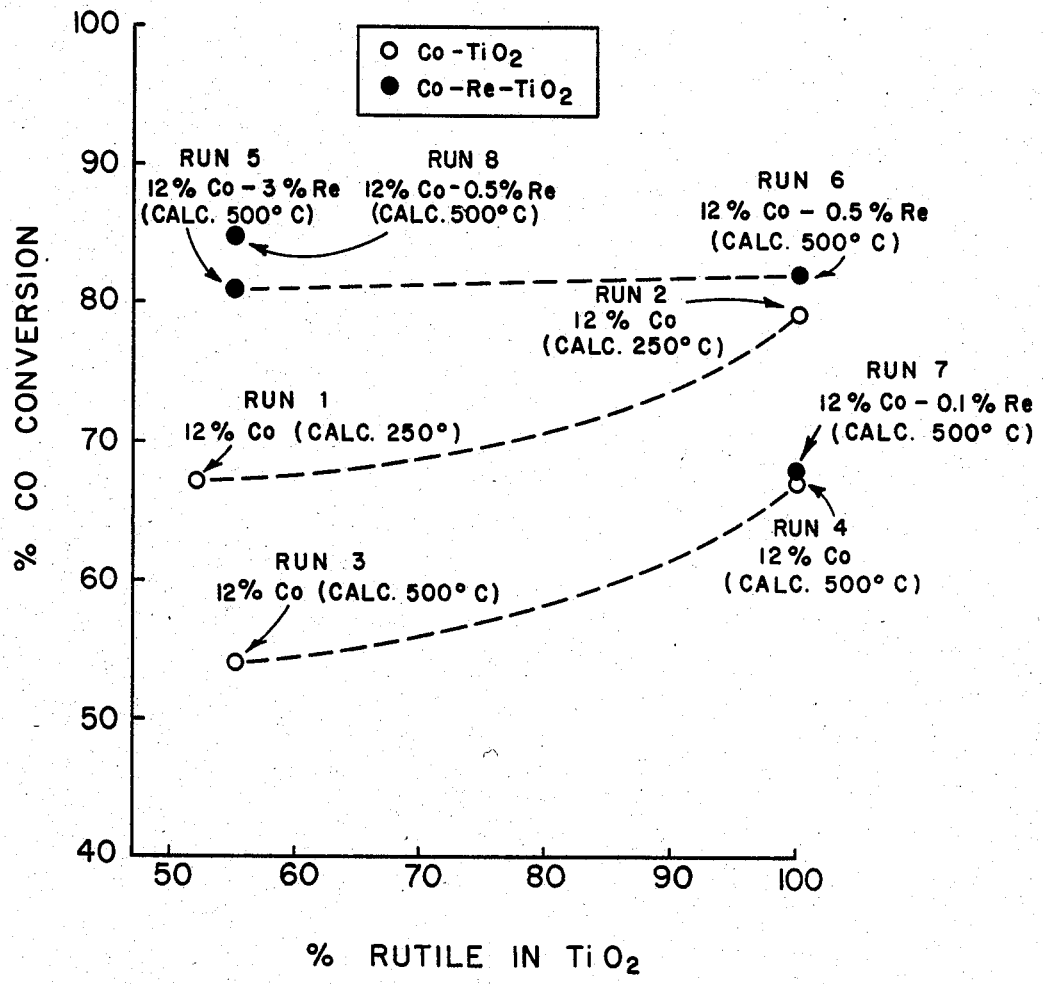

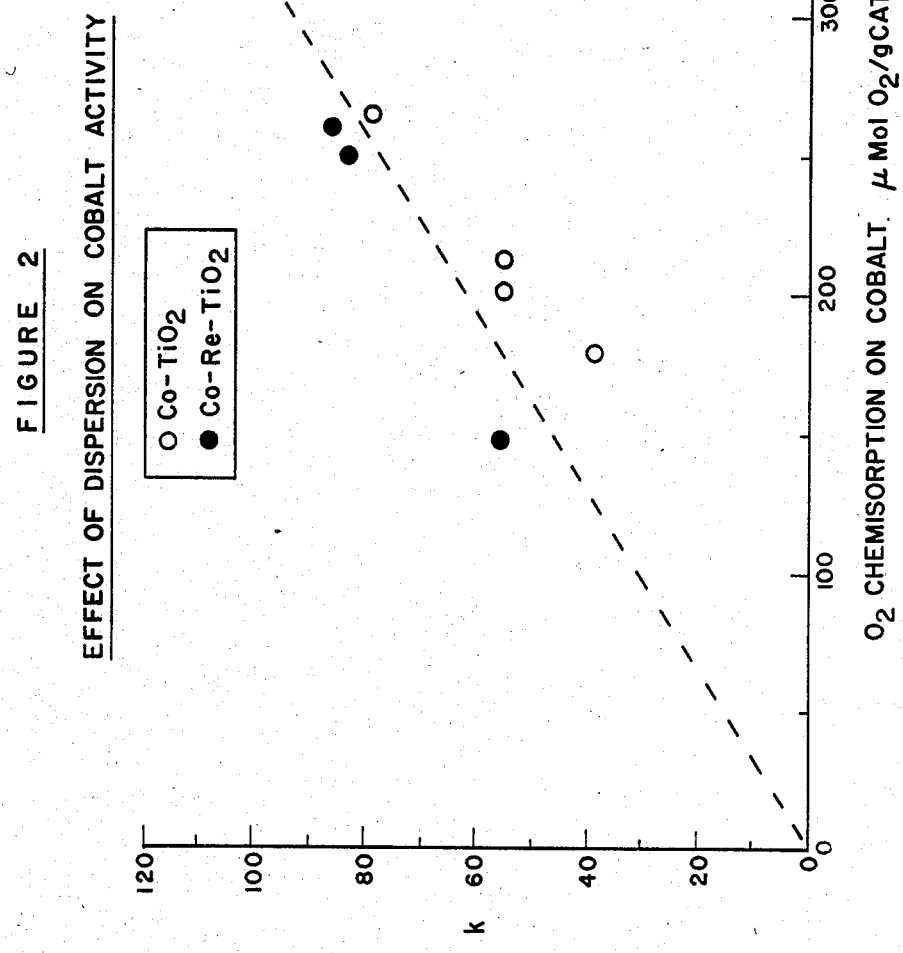

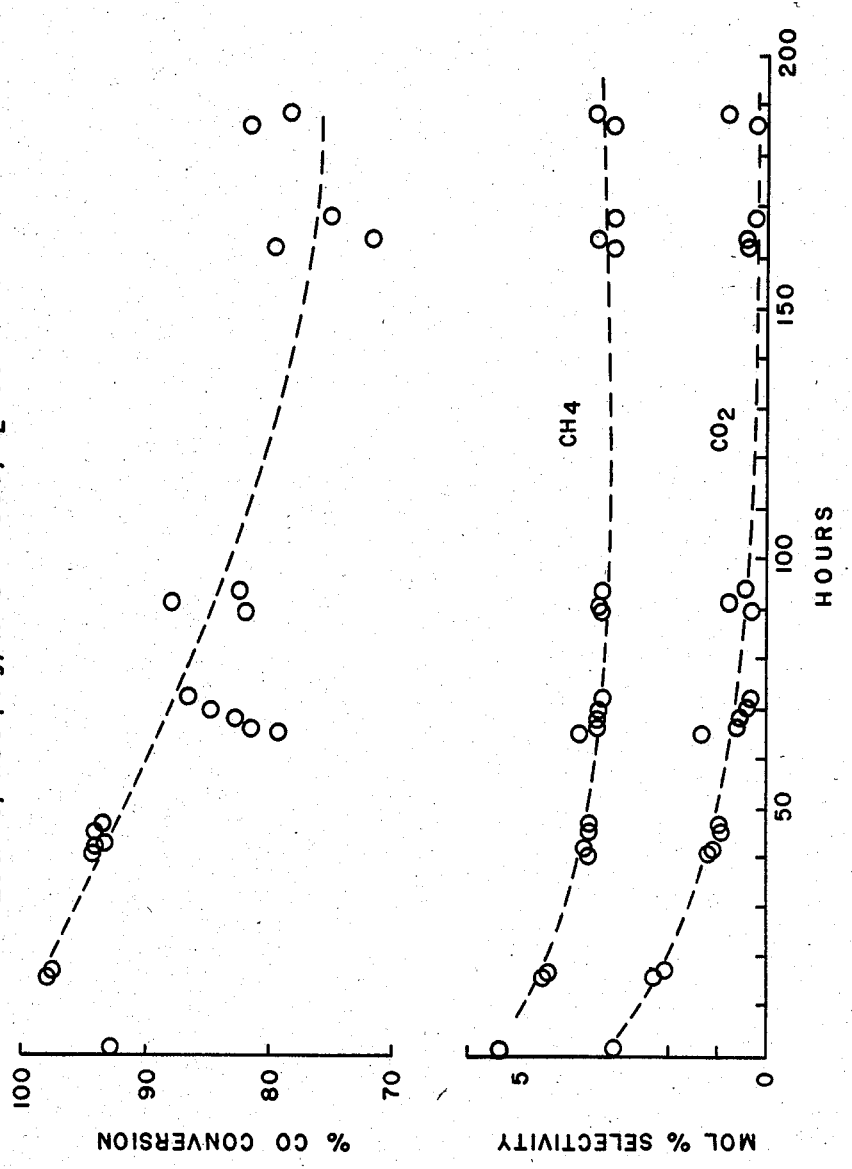

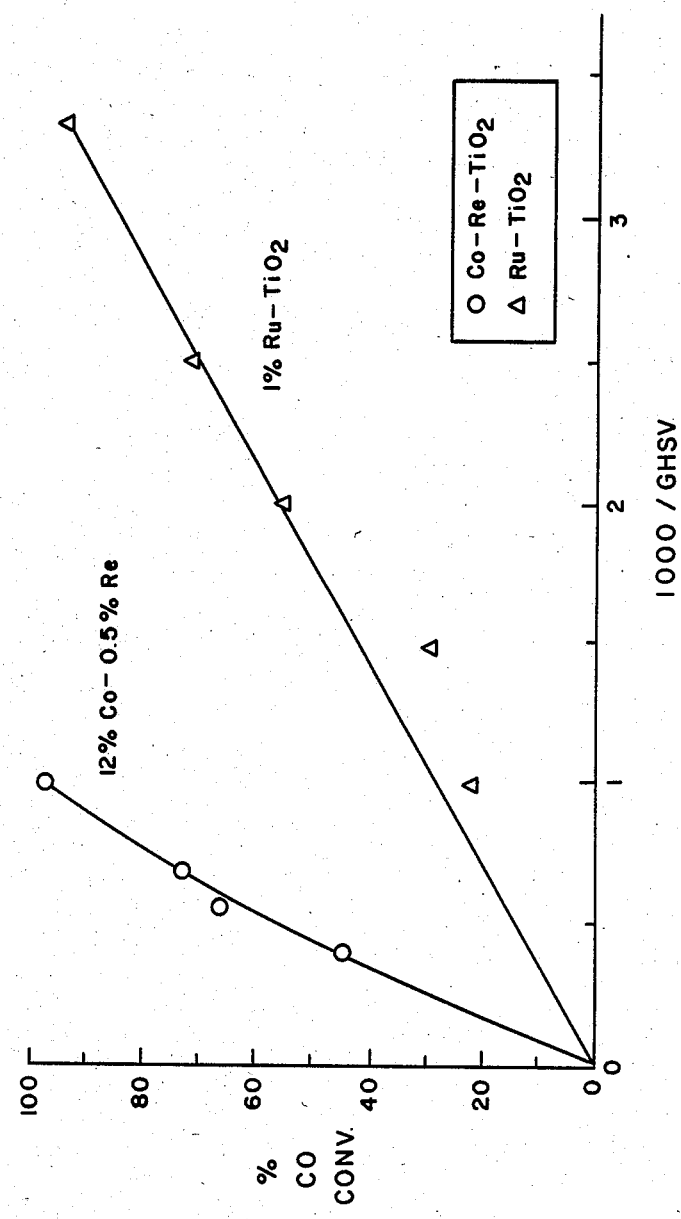

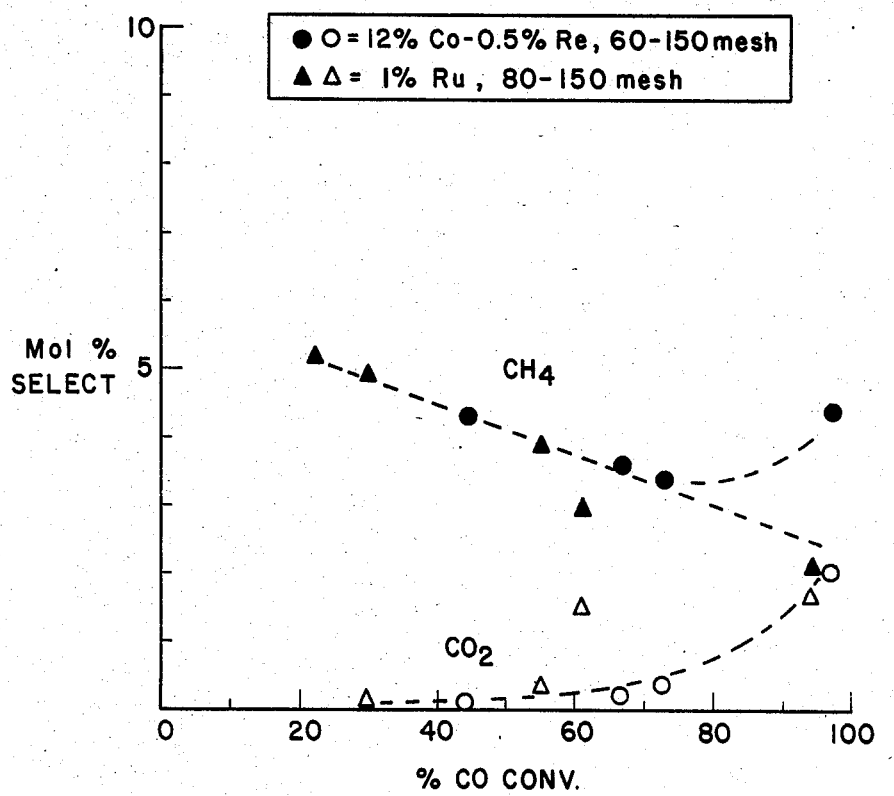

COBALT CATALYSTS FOR THE CONVERSION OF METHANOL TO HYDROCARBONS AND FOR FISCHER-TROPSCH SYNTHESIS

BACKGROUND OF THE INVENTION

I. Field of the Invention

This invention relates to improvements in a process for the conversion of methanol to hydrocarbons, to improvements in a Fischer-Tropsch process, and to improvements in Fischer-Tropsch catalysts. In particular, it relates to improved cobalt catalysts, and process for using such catalysts in the conversion of methanol, and Fischer-Tropsch synthesis to produce hydrocarbons, especially $C_{10}+$ distillate fuels, and other valuable products.

II. The Prior Art

Methane is often available in large quantities from process streams either as an undesirable by-product in admixture with other gases, or as an off gas component of a process unit, or units. More importantly, however, methane is the principle component of natural gas, and it is produced in considerable quantities in oil and gas fields. The existence of large methane, natural gas reserves coupled with the need to produce premium grade transportation fuels, particularly middle distillate fuels, creates a large incentive for the development of a new gas-to-liquids process. Conventional technology, however, is not entirely adequate for such purpose. Nonetheless, technology is available for the conversion of natural gas, to produce methanol, a product of currently limited market ability. However, to utilize the existing technology, there is a need for a process suitable for the conversion of methanol to high quality transportation fuels, particularly middle distillate fuels. On the other hand, the technology to convert natural gas, or methane, to synthesis gas is well established, and the conversion of the synthesis gas to hydrocarbons can be carried out via Fischer-Tropsch synthesis.

Fischer-Tropsch synthesis for the production of hydrocarbons from carbon monoxide and hydrogen is now well known in the technical and patent literature. The first commercial Fischer-Tropsch operation utilized a cobalt catalyst, though later more active iron catalysts were also commercialized. An important advance in Fischer-Tropsch catalysts occurred with the use of nickel-thoria on kieselguhr in the early thirties. This catalyst was followed within a year by the corresponding cobalt catalyst, $100Co:18ThO_2:100$ kieselguhr, parts by weight, and over the next few years by catalysts constituted to $100Co:18ThO_2:200$ kieselguhr and $100Co:5ThO_2:8MgO:200$ kieselguhr, respectively. The Group VIII non-noble metals, iron, cobalt, and nickel have been widely used in Fischer-Tropsch reactions, and these metals have been promoted with various other metals, and supported in various ways on various substrates. Most commercial experience has been based on cobalt and iron catalysts. The cobalt catalysts, however, are of generally low activity necessitating a multiple staged process, as well as low synthesis gas throughput. The iron catalysts, on the other hand, are not really suitable for natural gas conversion due to the high degree of water gas shift activity possessed by iron catalysts. Thus, more of the synthesis gas is converted to carbon dioxide in accordance with the equation: $H_2 + 2CO \rightarrow (CH_2)_x + CO_2$; with too little of the synthesis gas being converted to hydrocarbons and water as in the more desirable reaction, represented by the equation: $2H_2 + CO \rightarrow (CH_2)_x + H_2O$.

There exists a need in the art for a process useful for the conversion of methanol and synthesis gas at high conversion levels, and at high yields to premium grade transportation fuels, especially $C_{10}+$ distillate fuels; particularly without the production of excessive amounts of carbon dioxide.

III. Objects

It is, accordingly, a primary objective of the present invention to supply these needs.

A particular object is to provide novel catalysts, and process for the conversion of methanol and synthesis gas, i.e., carbon monoxide and hydrogen, respectively, to high quality distillate fuels characterized generally as admixtures of $C_{10}+$ linear paraffins and olefins.

A further and more specific object is to provide new and improved supported cobalt catalysts, notably cobalt-titania and cobalt-thoria-titania catalysts, which in methanol conversion reactions, and in Fischer-Tropsch synthesis and subsequent catalyst regeneration, are highly active, and exhibit high stability.

A yet further object is to provide a process which utilizes such catalysts for the preparation of hydrocarbons, notably high quality middle distillate fuels characterized generally as admixtures of linear paraffins and olefins, from methanol, or from a feed mixture of carbon monoxide and hydrogen via the use of such catalysts.

IV. The Invention

These objects and others are achieved in accordance with the present invention which, in general, embodies:

(A) A particulate catalyst composition constituted of a catalytically active amount of cobalt, or cobalt and thoria, to which is added sufficient rhenium to obtain, at corresponding process conditions, improved activity and stability in production of hydrocarbons from methanol, or in the production of hydrocarbons via carbon monoxide-hydrogen synthesis reactions than a catalyst composition otherwise similar except that it does not contain rhenium. Suitably, rhenium is added to the cobalt catalyst, or cobalt and thoria catalyst, in amount sufficient to form a catalyst having a rhenium:cobalt in weight ratio greater than about 0.010:1, preferably from about 0.025:1 to about 0.10:1. In terms of absolute concentrations, from about 0.05 percent to about 3 percent of rhenium, preferably from about 0.15 percent to about 1 percent of rhenium, based on the total weight of the catalyst composition (dry basis), is dispersed with the catalytically active amount of cobalt upon an inorganic oxide support, preferably upon titania ($TiO_2$), or a titania-containing support, particularly titania wherein the rutile:anatase weight ratio is at least about 2:3. This ratio is determined in accordance with ASTM D 3720-78: Standard Test Method for Ratio of Anatase to Rutile in Titanium Dioxide Pigments By Use of X-Ray Diffraction. Suitably, in terms of absolute concentrations the cobalt is present in the composition in amounts ranging from about 2 percent to about 25 percent, preferably from about 5 percent to about 15 percent, based on the total weight of the catalyst composition (dry basis), and sufficient rhenium is added to form a catalyst having a weight ratio of rhenium:cobalt greater than about 0.010:1, preferably from about 0.025:1 to about 0.10:1, based on the total weight of the cobalt and rhenium contained in the catalyst composition (dry basis). The absolute concentration of each metal is, of course, preselected to provide the desired ratio of rhenium:- cobalt, as heretofore expressed. Thoria can also be added to the composition, and is preferably added to the catalyst when it is to be used in the conversion of methanol. The thoria is dispersed on the support in amounts ranging from about 0.1 percent to about 10 percent, preferably from about 0.5 percent to about 5 percent, based on the total weight of the catalyst composition (dry basis). Suitably, the thoria promoted cobalt catalyst contains Co and $ThO_2$ in ratio of $Co:ThO_2$ ranging from about 20:1 to about 1:1, preferably from about 15:1 to about 2:1, based on the weight of the total amount of Co and $ThO_2$ contained on the catalyst. These catalyst compositions, it has been found, produce a product which is predominately $C_{10}+$ linear paraffins and olefins, with very little oxygenates. These catalysts provide high selectivity, high activity, and activity maintenance in methanol conversion, or in the conversion of the carbon monoxide and hydrogen to distillate fuels. These catalysts are also highly stable, particularly during high temperature air regenerations which further extend catalyst life.

(B) A process wherein the particulate catalyst composition of (A), supra, is formed into a bed, and the bed of catalyst contacted at reaction conditions with a methanol feed, or feed comprised of an admixture of carbon monoxide and hydrogen, or compound decomposable in situ within the bed to generate carbon monoxide and hydrogen, to produce a product of middle distillate fuel quality constituted predominately of linear paraffins and olefins, particularly $C_{10}+$ linear paraffins and olefins.

(i) In conducting the methanol reaction the partial pressure of methanol within the reaction mixture is generally maintained above about 100 pounds per square inch absolute (psia), and preferably above about 200 psia. It is preferable to add hydrogen with the methanol. Suitably methanol, and hydrogen, are employed in molar ratio of $CH_3OH:H_2$ above about 4:1, and preferably above 8:1, to increase the concentration of $C_{10}+$ hydrocarbons in the product. Suitably, the $CH_3OH:H_2$ molar ratio, where hydrogen is employed, ranges from about 4:1 to about 60:1, and preferably the methanol and hydrogen are employed in molar ratio ranging from about 8:1 to about 30:1. Inlet hydrogen partial pressures preferably range below about 80 psia, and more preferably below about 40 psia; inlet hydrogen partial pressures preferably ranging from about 5 psia to about 80 psia, and more preferably from about 10 psia to about 40 psia. In general, the reaction is carried out at liquid hourly space velocities ranging from about 0.1 $hr^{-1}$ to about 10 $hr^{-1}$, preferably from about 0.2 $hr^{-1}$ to about 2 $hr^{-1}$, and at temperatures ranging from about 150° C. to about 350° C., preferably from about 180° C. to about 250° C. Methanol partial pressures preferably range from about 100 psia to about 1000 psia, more preferably from about 200 psia to about 700 psia.

(ii) In general, the synthesis reaction is carried out at an $H_2:CO$ mole ratio of greater than about 0.5, and preferably the $H_2:CO$ mole ratio ranges from about 0.1 to about 10, more preferably from about 0.5 to about 4, at gas hourly space velocities ranging from about 100 V/Hr/V to about 5000 V/Hr/V, preferably from about 300 V/Hr/V to about 1500 V/Hr/V, at temperatures ranging from about 160° C. to about 290° C., preferably from about 190° C. to about 260° C., and pressures above about 80 psig, preferably ranging from about 80 psig to about 600 psig, more preferably from about 140 psig to about 400 psig. In its most preferred form, a bed of catalyst comprised of from about 5 percent to about 15 percent cobalt, containing sufficient rhenium to provide a catalyst containing rhenium:cobalt in ratio ranging from about 0.025:1 to about 0.10:1, is dispersed on titania, preferably a high purity titania, and a bed of such catalyst is contacted with a gaseous admixture of carbon monoxide and hydrogen, or compound decomposable in situ within the bed to generate carbon monoxide and hydrogen.

The product of either the methanol conversion reaction, or synthesis reaction generally and preferably contains 60 percent, more preferably 75 percent or greater, $C_{10}+$ liquid hydrocarbons which boil above 160° C. (320° F.).

It is found that cobalt and rhenium, or cobalt, thoria and rhenium, supported on titania, or other titania-containing support provides a catalyst system which exhibits superior methanol conversion, or hydrocarbon synthesis characteristics in Fischer-Tropsch reactions. The titania-containing supports used in the practice of this invention are preferably oxides having surface areas of from about 1 to about 120 $m^2g^{-1}$, preferably from about 10 to about 60 $m^2g^{-1}$.

Rhenium-cobalt/titania and rhenium-thoria-cobalt/titania catalysts exhibit high selectively in the conversion of methanol to hydrocarbon liquids, or synthesis of hydrocarbon liquids from carbon monoxide and hydrogen. The catalysts employed in the practice of this invention may be prepared by techniques known in the art for the preparation of other catalysts. The catalyst can, e.g., be prepared by gellation, or cogellation techniques. Suitably however the metals can be deposited on a previously pilled, pelleted, beaded, extruded, or sieved support material by the impregnation method. In preparing catalysts, the metals are deposited from solution on the support in preselected amounts to provide the desired absolute amounts, and weight ratio of the respective metals, or cobalt, rhenium, and thoria. Suitably, the cobalt and rhenium are composited with the support by contacting the support with a solution of a cobalt-containing compound, or salt, or a rhenium-containing compound, or salt, e.g., a nitrate, carbonate or the like. The thoria, where thoria is to be added, can then be composited with the support as a thorium compound or salt in similar manner, or the thorium can first be impregnated upon the support, followed by impregnation of the cobalt, or rhenium, or both. Optionally, the thorium and cobalt, or thoria, cobalt, and rhenium can be co-impregnated upon the support. The cobalt, rhenium and thorium compounds used in the impregnation can be any organometallic or inorganic compounds which decompose to give cobalt, rhenium, and thorium oxides upon calcination, such as a cobalt, rhenium, or thorium nitrate, acetate, acetylacetonate, naphthenate, carbonyl, or the like. The amount of impregnation solution used should be sufficient to completely immerse the carrier, usually within the range from about 1 to 20 times of the carrier by volume, depending on the metal, or metals, concentration in the impregnation solution. The impregnation treatment can be carried out under a wide range of conditions including ambient or elevated temperatures. Metal components other than rhenium and cobalt (or rhenium, cobalt and thorium) can also be added. The introduction of an additional metal, or metals, into the catalyst can be carried out by any method and at any time of the catalyst preparation, for example, prior to, following or simultaneously with the impregnation of the support with the cobalt and rhenium components. In the usual operation, the additional component is introduced simultaneously with the incorporation of the cobalt and rhenium, or cobalt, rhenium, and thorium components.

Titania is used as a support, or in combination with other materials for forming a support. The titania used for the support in either methanol or syngas conversions, however, is preferably one where the rutile:anatase ratio is at least about 2:3 as determined by x-ray diffraction (ASTM D 3720-78). Preferably, the titania used for the catalyst support of catalysts used in syngas conversion is one wherein the rutile:anatase ratio is at least about 3:2. Suitably the titania used for syngas conversions is one containing a rutile:anatase ratio of from about 3:2 to about 100:1, or higher, preferably from about 4:1 to about 100:1, or higher. A preferred, and more selective catalyst for use in methanol conversion reactions is one containing titania wherein the rutile:anatase ranges from about 2:3 to about 3:2. The surface area of such forms of titania are less than about 50 m²/g. This weight of rutile provides generally optimum activity, and $C_{10}+$ hydrocarbon selectivity without significant gas and $CO_2$ make.

The catalyst, after impregnation, is dried by heating at a temperature above about 30° C., preferably between 30° C. and 125° C., in the presence of nitrogen or oxygen, or both, or air, in a gas stream or under vacuum. It is necessary to activate the cobalt-titania, or thoria promoted cobalt-titania catalyst prior to use. Preferably, the catalyst is contacted with oxygen, air, or other oxygen-containing gas at temperature sufficient to oxidize the cobalt, and convert the cobalt to $Co_3O_4$. Temperatures ranging above about 150° C., and preferably above about 200° C. are satisfactory to convert the cobalt to the oxide, but temperatures up to about 500° C. such as might be used in the regeneration of a severely deactivated catalyst, can generally be tolerated. Suitably, the oxidation of the cobalt is achieved at temperatures ranging from about 150° C. to about 300° C. The cobalt, or cobalt and rhenium metals contained on the catalyst are then reduced. Reduction is performed by contact of the catalyst, whether or not previously oxidized, with a reducing gas, suitably with hydrogen or a hydrogen-containing gas stream at temperatures, above about 250° C.; preferably above about 300° C. Suitably, the catalyst is reduced at temperatures ranging from about b 250° C. to about 500° C., and preferably from about 300° C. to about 450° C., for periods ranging from about 0.5 to about 24 hours at pressures ranging from ambient to about 40 atmospheres. Hydrogen, or a gas containing hydrogen and inert components in admixture is satisfactory for use in carrying out the reduction.

If it is necessary to remove coke from the catalyst, the catalyst can be contacted with a dilute oxygen-containing gas and the coke burned from the catalyst at controlled temperature below the sintering temperature of the catalyst. The temperature of the burn is controlled by controlling the oxygen concentration and inlet gas temperature, this taking into consideration the amount of coke to be removed and the time desired to complete the burn. Generally, the catalyst is treated with a gas having an oxygen partial pressure of at least about 0.1 psi, and preferably in the range of from about 0.3 psi to about 2.0 psi to provide a temperature ranging from about 300° C. to about 550° C., at static or dynamic conditions, preferably the latter, for a time sufficient to remove the coke deposits. Coke burn-off can be accomplished by first introducing only enough oxygen to initiate the burn while maintaining a temperature on the low side of this range, and gradually increasing the temperature as the flame front is advanced by additional oxygen injection until the temperature has reached optimum. Most of the coke can be readily removed in this way. The catalyst is then reactivated, reduced, and made ready for use by treatment with hydrogen or hydrogen containing gas as with a fresh catalyst.

The invention will be more fully understood by reference to the following demonstrations and examples which present comparative data illustrating its more salient features. All parts are given in terms of weight except as otherwise specified. Feed compositions are expressed as molar ratios of the components.

BRIEF DESCRIPTION OF THE DRAWINGS

FIGS. 1 to 5 graphically depict data presented in the following examples.

The "Schulz-Flory Alpha" is a known method for describing the product distribution in Fischer-Tropsch synthesis reactions. The Schulz-Flory Alpha is the ratio of the rate of chain propagation to the rate of propagation plus termination, and is described from the plot of ln (Wn/n) versus n, where Wn is the weight fraction of product with a carbon number of n. In the examples below, an Alpha value was derived from the $C_{10}/C_{20}$ portion of the product. The Alpha value is thus indicative of the selectively of the catalyst for producing heavy hydrocarbons from the synthesis gas, and is indicative of the approximate amount of $C_{10}+$ hydrocarbons in the product. For example, a Schulz-Flory Alpha of 0.80 corresponds to about 35% by weight of $C_{10}+$ hydrocarbons in the product, a generally acceptable level of $C_{10}+$ hydrocarbons. A Schulz-Flory Alpha of 0.85, a preferred Alpha value, corresponds to about 54% by weight of $C_{10}+$ hydrocarbons in the products, and a Schulz-Flory Alpha of 0.90, a more preferred Alpha value, corresponds to about 74% by weight of $C_{10}+$ hydrocarbons in the product.

The following data show that the addition of a small amount of rhenium to a $Co-TiO_2$ catalyst maintains the cobalt in a high state of dispersion and stabilizes the catalyst during high temperature air treatment. The rhenium thus maintains the very high activity of the catalyst which is characteristic of one having well-dispersed cobalt on the $TiO_2$. The high activity of $Co-Re-TiO_2$ permits high conversion operations at low temperature where excellent selectivity is obtained in the conversion of syngas to $C_{10}+$ hydrocarbons.

EXAMPLE 1

Titania (Degussa P-25 $TiO_2$) was used as the support for all of the catalysts after mixing with sterotex, and after pilling, grinding, and screening to either 60-150 mesh or 16-20 mesh (Tyler). Two versions of $TiO_2$ were prepared by calcining portions of the $TiO_2$ in air at 500° C. and 600° C., respectively, overnight. This gave $TiO_2$ supports with the following properties:

| Calcination Temperature, °C. | Rutile:Anatase Weight Ratio[1] | Surface Area m²/g | Pore Volume ml/g |
|---|---|---|---|
| 500 | 1.2:1–1:1 | 33–36 | 0.28–0.40 |
| 600 | >30:1 | 10–16 | 0.11–0.15 |

[1]ASTM D 3720-78.

Catalysts, of 16–20 mesh size, were prepared from selected portions of these materials by simple impregnation of the support with cobaltous nitrate or perrhenic acid, or both, from acetone solution using a rotary evaporator, drying in a vacuum oven at 150° C., and calcining of the catalysts for three hours in flowing air in a quartz tube. The catalysts, identified in the second column of Table I, were charged to a reactor, reduced in $H_2$ at 450° C. for one hour, and then reacted with syngas at 200° C., 280 psig, GHSV=1000, and $H_2$:CO=2.15 for at least 16 hours. The performance of each catalyst was monitored by conventional GC analysis using neon as an internal standard (4% in the feed). Screening results for these catalysts and dynamic $O_2$ chemisorption data are given in Table I. Reference is also made to FIG. 1 which graphically depicts the data obtained with most of these catalysts, the percent CO conversion being plotted against the percent rutile contained in the $TiO_2$ support, the rutile:anatase ratio being expressed in both Table I and FIG. 1 as percent rutile to facilitate construction of the graph.

TABLE I

| Run No. | Wt. % Metals on 16–20 Mesh $TiO_2$ | % Rutile in $TiO_2$ | Air Treat °C. (3 hr.) | $O_2$ Chemisorption μ mol $O_2$/g Catalyst | % CO Conversion |
|---|---|---|---|---|---|
| | 280° C., 280 psig, GHSV = 1000, $H_2$:CO = 2.15 | | | | |
| 1 | 12 Co | 53[1] | 250 | 213 | 67 |
| 2 | 12 Co | 100[2] | 250 | 265 | 79 |
| 3 | 12 Co | 56[3] | 500 | 178 | 54 |
| 4 | 12 Co | 100[2] | 500 | 202 | 67 |
| 5 | 12 Co-3 Re | 56[3] | 500 | 399 | 81 |
| 6 | 12 Co-.5 Re | 100[2] | 500 | 285 | 82 |
| 7 | 12 Co-.1 Re | 100[2] | 500 | 145 | 67 |
| 8 | 12 Co-.5 Re | 56[3] | 500 | 343 | 85 |
| | 3 Re | 56[3] | 500 | 149 | <1 |

[1]Rutile:Anatase ratio 1.1:1.
[2]Rutile:Anatase ratio >30:1.
[3]Rutile:Anatase ratio 1.3:1.

Reference is made to the intermediate curve plotted on FIG. 1 which is representative of the data obtained from runs 1 and 2, of Table I representing an unpromoted 12% Co catalyst the $TiO_2$ support having a rutile:anatase ratio of 1.1:1 (53% rutile content), and another unpromoted 12% Co catalyst the support of which has a rutile:anatase ratio >30:1. The rutile:anatase ratio, as suggested, has been expressed in FIG. 1 as percentages for convenience of expression, or to facilitate construction of the graph. Both catalysts, represented on the graph by circled dots, were calcined in air at 250° C. Clearly the catalyst having the high rutile $TiO_2$ support is the superior catalyst providing 79% CO conversion vis-a-vis 67% CO conversion obtained by use of the catalyst having the lower rutile content $TiO_2$ support. Referring now to the bottom curve on the figure there is shown a plot representative of data obtained from runs 3 and 4, viz., runs made with unpromoted cobalt catalysts similar to those employed in runs 1 and 2, respectively, except that in these instances both catalyst were calcined in air at 500° C. These catalysts are also represented on the graph by circled dots. The unstabilized cobalt catalysts (as shown by a comparison of the activities of the catalysts used in runs 3 and 4, vis-a-vis those used in runs 1 and 2) both show a drop in activity due to the calcination in air at 500° C., which caused cobalt agglomeration, or loss of cobalt dispersion. The cobalt catalyst formed from a high rutile $TiO_2$ support is clearly the superior catalyst, the cobalt being more highly dispersed on the high rutile support.

Reference is again made to FIG. 1, runs 5, 6, and 8 (represented by black dots) being plotted as the top curve of the graphical data presented. Run 5 was made with a 12% C0-3% Re—$TiO_2$ (56% rutile), run 6 with a 12% Co-0.5 Re—$TiO_2$ (100% rutile), and run 8 with a 12% Co-0.5% Re—$TiO_2$ (56% rutile). These three catalysts were calcined in air at 500° C. These data clearly show that the rhenium was adequate to stabilize the cobalt metal on both of the catalysts against agglomeration, or loss of cobalt dispersion. A 0.5% level of rhenium is sufficient to stabilize the 12% Co catalyst (Runs 6 and 8) against loss of cobalt metal dispersion, it being noted that the rhenium promoted cobalt catalyst (Runs 5, 6, or 8) is at least the equivalent of or superior to the unpromoted cobalt wherein the cobalt is dispersed on a 100% $TiO_2$ rutile base.

Catalysts which contain at least 0.5% Re, as shown by the data, provide consistently high activity after 500° C. calcination regardless of rutile content. In general, there is no significant benefit obtained by adding a greater amount of rhenium. A 0.1 wt. % rhenium level, however, is inadequate to fully protect a 12% Co catalyst. Note that the rhenium promoted Co catalyst, 12% Co-0.1% Re catalyst (Run 7), is mildly agglomerated after contact with air at 500° C.

These activity data can also be expressed as a pseudo first order rate constant, k, represented by the equation $$k = \frac{GHSV}{P} \ln\left(\frac{1}{1-X}\right)$$

where X=fraction CO conversion, P=reactor pressure, atm., and GHSV=space velocity at ambient T and P, hr.$^{-1}$ A plot of k versus μ mol $O_2$/g catalyst, determined by conventional dynamic $O_2$ chemisorption, is shown by reference to FIG. 2. Note that for the Co—Re catalysts the contribution of $ReO_2$ chemisorption has been subtracted out of the total chemisorption value to obtain a chemisorption value for the cobalt component. The data fall on a straight line correlation thus indicating that the activity of all of these catalysts is a direct function of the cobalt dispersion. Rhenium promoted catalysts show the highest activity because they possess the highest cobalt dispersion. Such catalysts are also quite stable and have strongly resisted agglomeration during the 500° C. calcinations.

EXAMPLE 2

The surprisingly high activity of a Co—Re—$TiO_2$ catalyst is further demonstrated by a comparison of the 12% Co-0.5% Re—$TiO_2$ catalyst (100% rutile $TiO_2$) of Example 1 with a Ru—$TiO_2$ catalyst, a known high activity catalyst.

A 60–150 mesh granulated 12% Co-0.5% Re—$TiO_2$ (100% rutile) catalyst was charged to a reactor, and contacted with a syngas having an $H_2$:CO ratio of about 2 to 2.15 at 200° C., 280 psig, and GHSV=1000 for a period ranging up to 190 hours. For comparative purposes, a similar run was subsequently made with a 80-150 mesh granulated 1% Ru—TiO$_2$ (73% rutile; or 2.7:1 rutile:anatase) catalyst. Readings were taken at certain intervals, and the product stream analyzed to determine the wt. % CO conversion, and mol. % selectivity to CH$_4$, CO$_2$, C$_2$+ and the Schulz-Flory Alpha. Reference is made to Table II.

TABLE II

| | 12% Co—0.5% Re—TiO$_2$ 60-150 mesh, Calcined 500° C. | | | 1% Ru—TiO$_2$ 80-150 Mesh | |
|---|---|---|---|---|---|
| 200° C., 280 psig, GHSV = 1000, H$_2$/CO = 2.0-2.15 | | | | | |
| Hours on Stream | 15 | 75 | 190 | 4 | 162 |
| CO Conversion, wt. % | 98 | 86 | 78 | 45 | 22 |
| Mol. % Selectivity | | | | | |
| CH$_4$ | 4.5 | 3.5 | 3.3 | 2.3 | 5.2 |
| CO$_2$ | 2.3 | 0.6 | 0.3 | 2.3 | 0.1 |
| C$_2$+ | 93.2 | 95.9 | 96.4 | 95.4 | 94.7 |
| Schulz-Flory Alpha | — | 0.92 | 0.92 | — | — |

As shown by the data, the 12% Co-0.5% Re—TiO$_2$ catalyst is far more active than the 1% Ru—TiO$_2$ catalyst at 200° C., and is capable of providing high CO conversion and high selectivity to heavy hydrocarbons as indicated by the low CH$_4$+, CO$_2$ by-product yields and high Schulz-Flory Alpha.

The results of the continuous 190 hour run presented in Table II are graphically illustrated in FIG. 3. This high conversion run produced a very heavy hydrocarbon product consisting principally of linear paraffins with some linear olefins and branched components. The Schulz-Flory Alpha was 0.92, indicative of about 80 wt. % C$_{10}$+ hydrocarbons in the product.

During the course of the continuous runs, gas hourly space velocity was varied in order to obtain data at various levels of CO conversion. The results comparing the Co—Re—TiO$_2$ catalyst with the Ru—TiO$_2$ catalyst are graphically depicted in FIGS. 4 and 5. As shown in FIG. 4, the 12% Co-0.5% Re—TiO$_2$ catalyst is far more active than the 1% Ru—TiO$_2$ catalyst at 200° C., as determined by the higher conversion at a given space velocity. The selectivity for CH$_4$ and CO$_2$ is quite low for both of these catalysts as depicted by reference to FIG. 5.

EXAMPLE 3

Rhenium promoted cobalt catalysts are also very active for the conversion of methanol to hydrocarbons. For purpose of illustration, a series of runs were made with three cobalt catalysts, viz., (1) 12% Co-2% ThO$_2$/TiO$_2$, (2) 12% Co-2% ThO$_2$-0.5% Re/TiO$_2$, and (3) 12% Co-0.5 Re/TiO$_2$, formed by impregnation of 16-20 mesh TiO$_2$ (56% rutile). Each catalyst was charged to the reactor and air calcined at 500° C. In conducting the runs, methanol, with argon, was passed over each of the catalysts at 230° C., 400 psig, GHSV=500, and CH$_3$OH/Ar=4 with the results obtained by reference to Table III.

TABLE III

| Methanol Conversion 230° C., 400 psig, GHSV = 500, CH$_3$OH/Ar = 4 (16-20 Mesh Catalysts, Calcined 500° C.) | | | |
|---|---|---|---|
| | 12% Co— 2% ThO$_2$ | 12% Co— 2% ThO$_2$— 0.5% Re | 12% Co— 0.5% Re |
| CH$_3$OH Conversion | 49 | 100 | 87 |
| Carbon Product Distribution, Wt. % | | | |
| CO | 6 | 2 | 2 |
| CO$_2$ | 14 | 28 | 22 |
| CH$_4$ | 6 | 14 | 9 |
| C$_2$+ | 74 | 56 | 67 |

These data clearly show that the Co—Re—TiO$_2$ and Co—ThO$_2$—Re—TiO$_2$ catalysts provide high levels of conversion compared to the unpromoted Co—ThO$_2$—TiO$_2$ catalyst, a preferred catalyst for this reaction, although selectivities to C$_2$+ hydrocarbons in each instance is debited to some extent by a high CO$_2$ make. This high water gas shift activity with methanol is not observed with a syngas feed.

The following data show that the cobalt catalysts are activated for syngas conversion by reducing the cobalt prior to use of the catalyst for the conversion of syngas to hydrocarbons.

EXAMPLE 4

A series of runs were made at similar conditions with portions of a Co—TiO$_2$ catalyst (12% Co-0.5% Re/TiO$_2$ (100% rutile) after pretreatment of the different portions for three hours with hydrogen at 200° C., 235° C., 300° C., and 450° C., respectively. The runs were carried out by contact of the catalysts, in different runs at 200° C., 280 psig. GHSV=1000 and H$_2$:CO=2.15, with a synthesis gas comprised of an admixture of hydrogen and carbon monoxide. The results are given in Table IV.

TABLE IV

| 12% Co-0.5% Re—Rutile, 60-150 Mesh, Calcined 500° C. - 3 Hr. 200° C., 280 psig, GHSV = 1000, H$_2$/CO = 2.15 | |
|---|---|
| Reduction Temperature, °C. | CO Conversion |
| 200 | 0 |
| 235 | 8 |
| 300 | 98 |
| 450 | 99 |

The results show that the high temperature reduction is necessary to activate the catalyst for conversion of syngas. Reduction of the cobalt above about 250° C., and preferably above about 300° C. is necessary. Suitably, the reduction is carried out at temperatures ranging from about 250° C. to about 500° C., and preferably from about 300° C. to about 450° C., with hydrogen or a hydrogen-containing gas.

It is apparent that various modifications and changes can be made without departing the spirit and scope of the present invention.

What is claimed is:

1. A catalyst useful for the conversion at reaction conditions of methanol or synthesis gas to hydrocarbons by contact with a catalyst which comprises cobalt and thoria in catalytically active amounts, and rhenium, composited with an inorganic oxide support in weight ratio of rhenium:cobalt ranging from about 0.025:1 to about 0.10:1.

2. The composition of claim 1 wherein the catalyst contains from about 2 percent to about 25 percent cobalt, based on the weight of the catalyst composition.

3. The composition of claim 2 wherein the catalyst contains from about 5 to about 15 percent cobalt, based on the weight of the catalyst composition.

4. A catalyst useful for the conversion at reaction conditions of methanol or synthesis gas to hydrocarbons by contact with a catalyst which comprises rhenium, cobalt, and thoria in catalytically active amounts composited with an inorganic oxide support, the catalyst containing from about 2 percent to about 25 percent cobalt, and from about 0.1 percent to about 10 percent thoria, based on the total weight of the catalyst, the weight ratio of rhenium:cobalt ranging from about 0.025:1 to about 0.10:1, and the ratio of cobalt:thoria ranging from about 20:1 to about 1:1.

5. The composition of claim 4 wherein the catalyst comprises from about 5 percent to about 15 percent cobalt, and from about 0.5 percent to about 5 percent thoria.

6. The composition of claim 4 wherein the inorganic oxide support is titania or a titania-containing support.

7. The composition of claim 6 wherein the rutile:anatase content of the titania is at least about 2:3.

8. A catalyst useful for the conversion at reaction conditions of methanol or synthesis gas to hydrocarbons by contact with a catalyst which comprises from about 2 percent to about 25 percent cobalt, and rhenium, composited with titania or a titania-containing support, the weight ratio of rhenium:cobalt ranging from about 0.025:1 to about 0.10:1.

9. The composition of claim 8 wherein the catalyst comprises rhenium, cobalt, and thoria dispersed on the support, the catalyst containing from about 0.1 percent to about 10 percent thoria, based on the total weight of the catalyst.

10. The composition of claim 8 wherein the rutile:anatase content of the titania is at least about 2:3.

11. The composition of claim 8 wherein the rutile:anatase content of the titania ranges from about 3:2 to about 100:1, or higher.

12. The composition of claim 9 wherein the ratio of cobalt:thoria ranges from about 20:1 to about 1:1.

13. The composition of claim 9 wherein the weight ratio of cobalt:thoria ranges from about 15:1 to about 2:1.

14. The composition of claim 9 wherein the catalyst contains from about 5 to about 15 percent cobalt, based on the weight of the catalyst composition.

15. A catalyst useful for the conversion at reaction conditions of methanol or synthesis gas to hydrocarbons by contact with a catalyst which comprises from about 2 percent to about 25 percent cobalt, from about 0.1 percent to about 10 percent thoria, based on the total weight of the catalyst, and rhenium, composited with titania or a titania-containing support, the weight ratio of rhenium:cobalt ranging from about 0.025:1 to about 0.10:1, and the rutile:anatase content of the titania is at least about 2:3.

16. The composition of claim 15 wherein the rutile:anatase content of the titania ranges from about 3:2 to about 100:1, or greater.

17. The composition of claim 15 wherein the ratio of cobalt:thoria ranges from about 20:1 to about 1:1.

18. The composition of claim 15 wherein the weight ratio of cobalt:thoria ranges from about 15:1 to about 2:1.

19. The composition of claim 15 wherein the catalyst contains from about 5 to about 15 percent cobalt, based on the weight of the catalyst composition.

20. A catalyst useful for the conversion at reaction conditions of methanol or synthesis gas to hydrocarbons by contact with a catalyst which comprises a catalytically active amount of cobalt, and rhenium, composited with titania or a titania-containing support, the weight ratio of rhenium:cobalt ranging from about 0.025:1 to about 0.10:1.

* * * * *